(12) United States Patent
Chang

(10) Patent No.: US 9,027,187 B2
(45) Date of Patent: May 12, 2015

(54) CLEANING SYSTEM

(71) Applicant: Hon Hai Precision Industry Co., Ltd., New Taipei (TW)

(72) Inventor: Jen-Tsorng Chang, New Taipei (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 0 days.

(21) Appl. No.: 13/961,898

(22) Filed: Aug. 8, 2013

(65) Prior Publication Data

US 2014/0283316 A1    Sep. 25, 2014

(30) Foreign Application Priority Data

Mar. 25, 2013    (TW) .............................. 102110558 A

(51) Int. Cl.
| | |
|---|---|
| *A47L 13/40* | (2006.01) |
| *B08B 5/02* | (2006.01) |
| *B08B 6/00* | (2006.01) |
| *B08B 15/04* | (2006.01) |
| *G01N 21/15* | (2006.01) |
| *G02B 27/00* | (2006.01) |

(52) U.S. Cl.
CPC ... *B08B 5/02* (2013.01); *B08B 6/00* (2013.01); *B08B 15/04* (2013.01); *G01N 21/15* (2013.01); *G02B 27/0006* (2013.01)

(58) Field of Classification Search
USPC ............................................ 15/1.51, 302, 345
IPC ....................................... A47L 5/38,5/14, 13/40
See application file for complete search history.

(56) References Cited

U.S. PATENT DOCUMENTS 7,047,984 B2 *    5/2006    Blattner et al. ................ 134/1.3

* cited by examiner

*Primary Examiner* — David Redding
(74) *Attorney, Agent, or Firm* — Novak Druce Connolly Bove + Quigg LLP

(57) ABSTRACT

A cleaning system used for removing contaminant particles on a surface of an image sensor is provided. The cleaning system includes an gas blower, two plate electrodes parallel to each other, and a high frequency voltage source. The gas blower supplies a mixed gas to the two plate electrodes. The high frequency voltage source provides a high voltage for the two plate electrodes to ionize the mixed gas, thereby the ionized gas cause contaminant particles on the surface of the image sensor to be positively charged, and cause the surface of the image sensor to be positively charged. The vacuum pump device removes the positively charged particles, which are repelled by the positively charged surface of the image sensor.

3 Claims, 1 Drawing Sheet

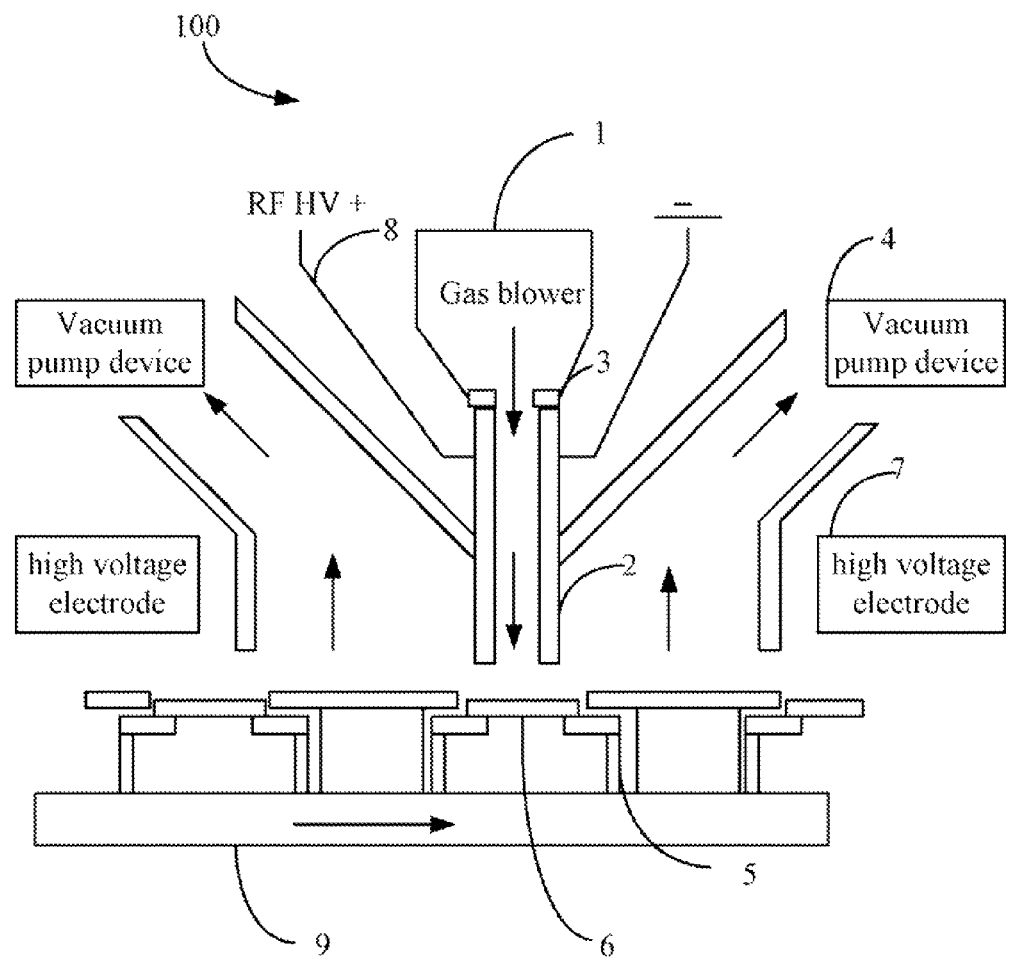

CLEANING SYSTEM

BACKGROUND

1. Technical Field

The present disclosure relates to cleaning systems, and particularly to an gas cleaning system for removing contaminant particles on a surface of an image sensor.

2. Description of Related Art

Image sensors must be protected against contamination by external agents, such as dust and humidity, which could lead to irreparable damage. A user usually manually wipes a surface of an image sensor to protect the image sensor. However, it is time-consuming and inconvenient for the user.

Therefore, what is needed is a cleaning system to overcome the above described limitations.

BRIEF DESCRIPTION OF THE DRAWING

The FIGURE is a schematic diagram of a cleaning system in accordance with an exemplary embodiment.

DETAILED DESCRIPTION

The FIGURE shows an gas cleaning system 100 of an embodiment. In the embodiment, the gas cleaning system 100 is used for removing contaminant particles on a surface of an image sensor 6. The cleaning system 100 includes a gas blower 1, two plate electrodes 2 parallel to each other, two electromagnetic valves 3 arranged between the gas blower 1 and the two plate electrodes 2, a high frequency voltage source 8, two vacuum pump devices 4 arranged adjacent to the two plate electrodes 2, and two high voltage electrodes 7 arranged adjacent to the two vacuum pump devices 4. The plate electrodes 2 cooperatively defines a gas channel for allowing the mixed gas to pass therethrough.

A transmission belt 9 is movably placed below the two plate electrodes 2. The transmission belt 9 includes a number of support portions 5. Each of the support portions 5 supports an optical sensor 6. The two plate electrodes 2 are aligned with one of the support portions 5.

The gas blower 1 blows a mixed gas to the two plate electrodes 2. In one embodiment, the mixed gas includes oxygen and argon. The two electromagnetic valves 3 cooperate to control a flow rate of the mixed gas from the gas blower 1 to the gas channel of the two plate electrodes 2. The high frequency voltage source 8 apply a voltage to the two plate electrodes 2 to ionize the mixed gas, thereby the ionized mixed gas cause contaminant particles on the surface of the image sensor to be positively charged, and cause the surface of the image sensor to be positively charged. The two vacuum pump device 4 removes the positively charged particles, which are repelled by the positively charged surface of the image sensor 6. However, when the two vacuum pump device 4 remove the positively charged particles, external air will be introduced to stain the optical sensor 6 again. The two high voltage electrodes 7 ionize the external air introduced by the vacuum pump devices 4. The two vacuum pump devices 4 remove the ionized air, thereby preventing the optical sensor 6 from being stained by the external air.

After one of the optical sensors 6 is cleaned, the transmission belt 9 is moved to allow a next support portion 5 to align with the two plate electrodes 2, thereby cleaning a next optical sensor supported by the next support portion 5.

Although various embodiments have been specifically described, the disclosure is not to be construed as being limited thereto. Various changes or modifications may be made to the embodiments without departing from the scope and spirit of the disclosure.

What is claimed is:

1. A cleaning system for removing contaminant particles on a surface of an image sensor, comprising:
   a gas blower configured to blow a mixed gas;
   two plate electrodes parallel to each other, the plate electrodes cooperatively defining a gas channel for allowing the mixed gas to pass therethrough;
   a high frequency voltage source configured to apply a high voltage to the two plate electrodes to ionize the mixed gas, thereby the ionized gas cause contaminant particles on the surface of the image sensor to be positively charged, and cause the surface of the image sensor to be positively charged;
   a vacuum pump device arranged adjacent to the two plate electrodes, and configured to remove the positively charged particles, which are repelled by the positively charged surface of the image sensor; and
   at least one high voltage electrode arranged adjacent to the vacuum pump device, and configured to ionize external air introduced by the vacuum pump device; wherein
   the vacuum pump device is further configured to remove the ionized air.

2. The cleaning system as described in claim 1, further comprising:
   two electromagnetic valves arranged between the gas blower and the two plate electrodes, and configured to control a flow rate of the mixed gas from the gas blower to the gas channel of the two plate electrodes.

3. The cleaning system as described in claim 1, wherein the mixed gas comprises oxygen and argon.

* * * * *